(12) United States Patent
Tufi

(10) Patent No.: US 9,233,051 B2
(45) Date of Patent: Jan. 12, 2016

(54) BLISTER HOLDER PROVIDED WITH MEANS DESIGNED TO DETECT THE NUMBER OF EXTRACTED PRODUCTS FROM THE BLISTER AND WITH GSM/GPRS COMMUNICATION MEANS TO REMOTELY DIALOGUE WITH A CONTROL CENTER

(76) Inventor: Osvaldo Tufi, Rome (IT)

( * ) Notice: Subject to any disclaimer, the term of this patent is extended or adjusted under 35 U.S.C. 154(b) by 211 days.

(21) Appl. No.: 13/985,937

(22) PCT Filed: Feb. 16, 2012

(86) PCT No.: PCT/IT2012/000048
§ 371 (c)(1),
(2), (4) Date: Aug. 16, 2013

(87) PCT Pub. No.: WO2012/111034
PCT Pub. Date: Aug. 23, 2012

(65) Prior Publication Data
US 2013/0319902 A1 Dec. 5, 2013

(30) Foreign Application Priority Data
Feb. 16, 2011 (IT) .............................. RM2011A0072

(51) Int. Cl.
*G08B 23/00* (2006.01)
*A61J 7/04* (2006.01)
*A61J 1/03* (2006.01)
*B65D 83/04* (2006.01)

(52) U.S. Cl.
CPC .. *A61J 7/04* (2013.01); *A61J 1/035* (2013.01); *A61J 7/0409* (2013.01); *B65D 83/0463* (2013.01); *A61J 7/0436* (2015.05); *A61J 2200/30* (2013.01)

(58) Field of Classification Search
CPC .......... A61J 1/035; A61J 2200/30; A61J 7/07
USPC ...................................................... 340/573.1
See application file for complete search history.

(56) References Cited

U.S. PATENT DOCUMENTS

| 4,660,991 A | 4/1987 | Simon |
| 5,412,372 A * | 5/1995 | Parkhurst et al. .......... 340/568.1 |

(Continued)

FOREIGN PATENT DOCUMENTS

| EP | 0 009 280 | 4/1980 |
| JP | 3 256876 | 11/1991 |
| WO | 2004/002396 | 1/2004 |

OTHER PUBLICATIONS

International Search Report dated May 16, 2012, corresponding to PCT/IT2012/000048.

*Primary Examiner* — Steven Lim
*Assistant Examiner* — Omeed Alizada
(74) *Attorney, Agent, or Firm* — Young & Thompson

(57) ABSTRACT

A pocket-sized blister-pack case, designed to receive a blister pack of a known type with a plurality of cells each containing a product, for example a pharmaceutical product in the form of a pill or tablet, has a plurality of capacitive and/or optical sensors for counting and displaying the number of pills that are taken out of the respective cell, as likewise the date and time of when they were taken, and is able to communicate via a packet mobile-radio interface the data to an authorized remote control centre that can check the degree of compliance of the patient to the therapy prescribed and can dialogue with the patient himself via packet and/or circuit mobile-radio interface.

13 Claims, 15 Drawing Sheets

(56) References Cited

U.S. PATENT DOCUMENTS

| | | |
|---|---|---|
| 5,752,621 A | 5/1998 | Passamante |
| 8,688,468 B1 * | 4/2014 | daCosta et al. ............... 705/2 |
| 2005/0162979 A1 * | 7/2005 | Ostergaard et al. ............ 368/10 |
| 2006/0058917 A1 | 3/2006 | Vonk et al. |

* cited by examiner

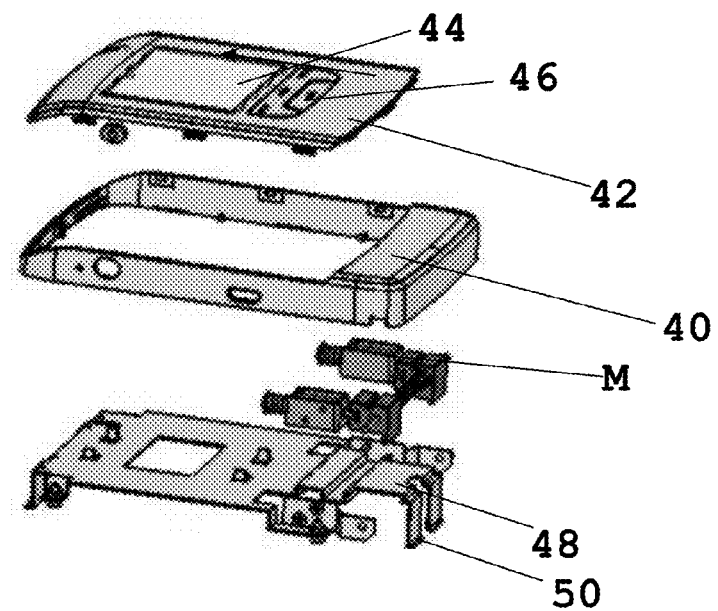
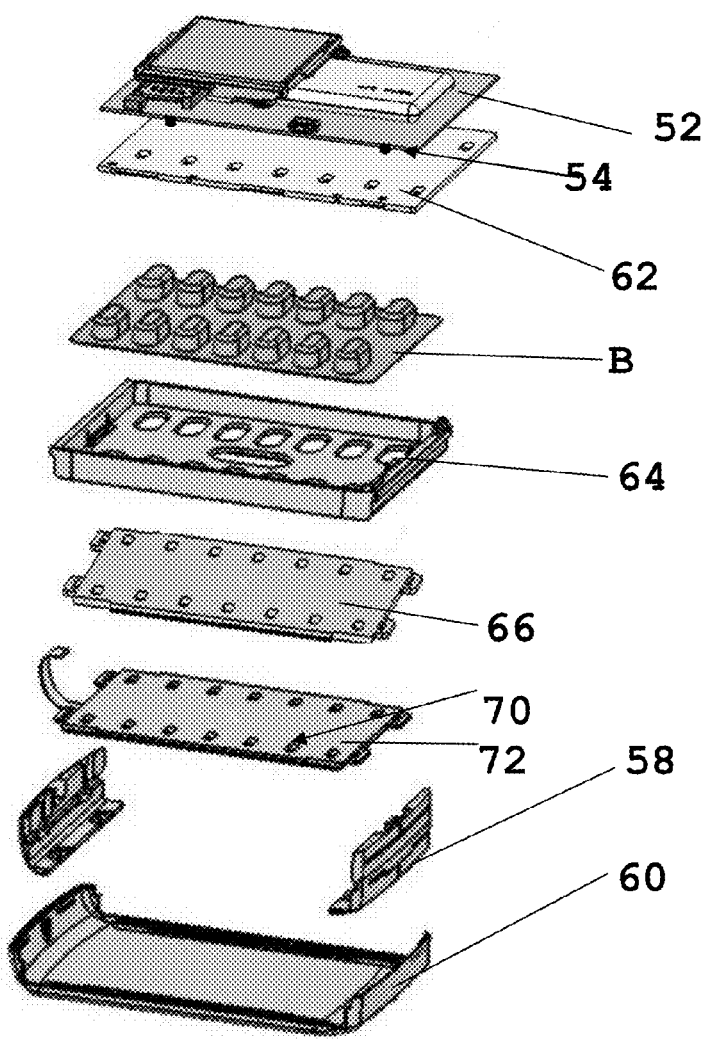
Fig. 15

BLISTER HOLDER PROVIDED WITH MEANS DESIGNED TO DETECT THE NUMBER OF EXTRACTED PRODUCTS FROM THE BLISTER AND WITH GSM/GPRS COMMUNICATION MEANS TO REMOTELY DIALOGUE WITH A CONTROL CENTER

The present invention relates to an innovative blister holder or blister-pack case that enables a person to keep under control the number of products that have been effectively taken out of the blister pack, and moreover to communicate remotely the data collected to an authorized control centre.

In particular, the blister-pack case is designed for the pharmaceutical sector in so far as it enables a patient under pharmacological therapy to visualize the number of pills that have been taken out of the blister pack, as likewise the date and time when they were assumed, and to communicate said data to an authorized centre that can check the degree of compliance of the patient to the therapy prescribed.

The term "blister pack" identifies various types of plastic packages pre-produced and used as containers of small objects, in particular pharmaceutical products in the form of tablets, pills, or the like. Each package comprises a plurality of cavities or cells made in a substrate of sheet plastic material or aluminium, which are each designed to contain a single pill or tablet and are closed by a foil, normally of aluminium, that can be pushed through.

The blister pack is opened by pressing a finger against the individual deformable cavity or cell: the pressure, exerted on the aluminium foil by the finger, via the object contained in the cell, pushes the product through said foil.

With the blister packs present on the market, thanks to the fact that the pack is transparent, the user has the possibility of visualizing and easily keeping track of the doses taken and the ones still present in the pack.

There remains, however, unsolved the problem of checking, above all in chronic therapies or in therapies that use latest-generation molecules that require a precise control of dosage, patient compliance in regards the medical prescription.

Consider, by way of example, a subject who must assume periodically a particular drug. It is evident that it may happen that, during the period where said drug has to be taken, said subject can forget to assume the exact dosage of the drug and/or not remember when he/she last took it.

Consequently, there is markedly felt the need for a blister-pack case that will advantageously enable improvement of the therapeutic effectiveness through an accurate monitoring of the modalities of assumption of the drug, counting the number of pills taken out of the blister pack and the date and time of assumption, and helping the patient to visualize said information and to transmit it remotely to a structure authorized for control of patient compliance.

The task of the present invention is consequently to overcome said drawback by proposing a blister-pack case in the form of a pocket container, designed to house the blister pack inside it, provided in which are:

means for detecting that the blister pack has been inserted properly in the blister-pack case;

means for detecting extraction of each product from the blister pack itself via opening and closing of a drawer from which the pill is to be taken;

means for detecting the presence/absence, in the blister pack, of each individual product;

a central processing unit designed to process the signals coming from said detection means, count the number of products taken out, and check the patient compliance to the therapy on the basis of the date and time of assumption;

a display, which, in addition to having mainly the function of LED to warn the user that it is time to assume a product, enables display, by receiving data from said central processing unit, of said number of the products taken out and other information, such as date and time of assumption, and stores said information in an internal memory of the blister-pack case;

a internal memory of the blister-pack case for storing the data processed by said central processing unit; and means for recalling on the display, using a purposely provided key, the data regarding the last time the product was taken and the data regarding patient compliance.

By the term "product" is meant herein generically an individual dose of a product, which in the specific case of a drug assumes the form of pills, tablets, lozenges, or capsules. For simplicity, in the ensuing description, the term "tablet or pill" will consequently be used, without, however, this implying any limitation of the invention to these two typical forms.

In a first embodiment to be used with a blister pack totally made of aluminium, the container is equipped with a lid and a drawer for taking out the tablet or pill, and the means for detecting the presence/absence in the blister pack of each individual tablet or pill are of a capacitive type and are housed within said lid, whereas counting of the tablets or pills taken out is performed by the CPU only after both the drawer and the lid have returned into their initial configuration, i.e., the closed configuration. In this way, the display shows the updated data of the tablets or pills taken out only when the blister-pack case is closed.

In a second embodiment to be used with a plastic blister pack closed by an aluminium foil, the container is without a lid and has a sliding drawer that can be opened on either side, and the means for detecting the presence/absence in the blister pack of each individual tablet or pill are of an optical type and comprise:

a fixed array of sensing LEDs, preferably LEDs that adopt SMD (Surface Mounting Device) technology, said array being mounted on the bottom surface of the electronic card of the blister-pack case that is positioned in the container on the roof of the blister pack in such a way that to each LED of the array there corresponds an individual pill of the blister pack;

a light diffuser, such as for example a semitransparent glass underlying the blister pack;

a certain number of emitting LEDs underlying or set laterally with respect to said glass;

a reflecting lamina designed to reflect the light emitted by the emitting LEDs in the direction of the blister pack; and a charge-pump circuit connected to said emitting LEDs for generating a flash light in such a way that, in the event of absence of a tablet, the passage of light will cause in the sensing LEDs the emission of a current pulse that can be detected by a micro-controller.

Advantageously, the CPU on the electronic card disables each sensing LED after the corresponding tablet has been taken.

An alternative to the optical system just described to be used in the presence of blister packs with cells made of transparent or semitransparent material (and hence not aluminium), envisages laying the blister pack in a drawer with a perforated bottom that is able to slide inside the container between an underlying fixed array of receiving sensors and an overlying array of infrared LEDs. Also in this case, the presence of a hinged lid is superfluous, and this enables a considerable reduction in the thickness of the container itself. In this embodiment, the container is equipped with a top display, appearing on which is the number of capsules or pills that, once the drawer has been pulled out, are expelled from the blister pack and dropped directly into the patient's hand, thanks to the pulse emitted by the underlying receiving sensor, which perceives the light signal emitted by the top LED through the blister pack when the pill or capsule has left its cell.

Advantageously, in order to reduce the travel of the drawer, the latter can be pulled out by being slid in either direction. For this purpose, two motors are provided for opening to the right and opening to the left that may be activated automatically or controlled via a pushbutton.

According to a peculiar characteristic of the invention, whatever the system of detection of the presence/absence of the pill/capsule, the data stored in the memory of the blister-pack case can be transmitted automatically via a GSM/GPRS module to an external structure authorized for carrying out checks, such as a Customer Service that can in turn dialogue with the patient via packet mobile-radio interface (e.g. GPRS, HSPA, HSPA+, LTE) and/or via circuit mobile-radio interface. Reception of the SMS by the Customer Service takes place in real time.

The blister-pack case with this technology becomes a bi-directional communication channel proper between the patient and the Customer Service, with the functions of an ordinary mobile phone, equipped with photographic camera and/or video camera.

According to another variant, the check can be made also by a doctor, who can download onto his PC, thanks to the presence on the device forming the subject of the invention of a USB port, all the data regarding assumption of the medicine by the patient.

In another variant embodiment there are moreover provided:

means for requesting from the control centre a visit by one of their nurses at the patient's home; and means for sending a signal of confirmation of the fact that the patient has fulfilled a particular request made by the control centre.

A better understanding of the invention will be obtained from the ensuing detailed description with reference to the attached drawings, which show, purely by way of example, some preferred embodiments.

In the drawings:

FIG. 15 is an exploded view of the entire blister-pack case of FIG. 14.

Figure 10:
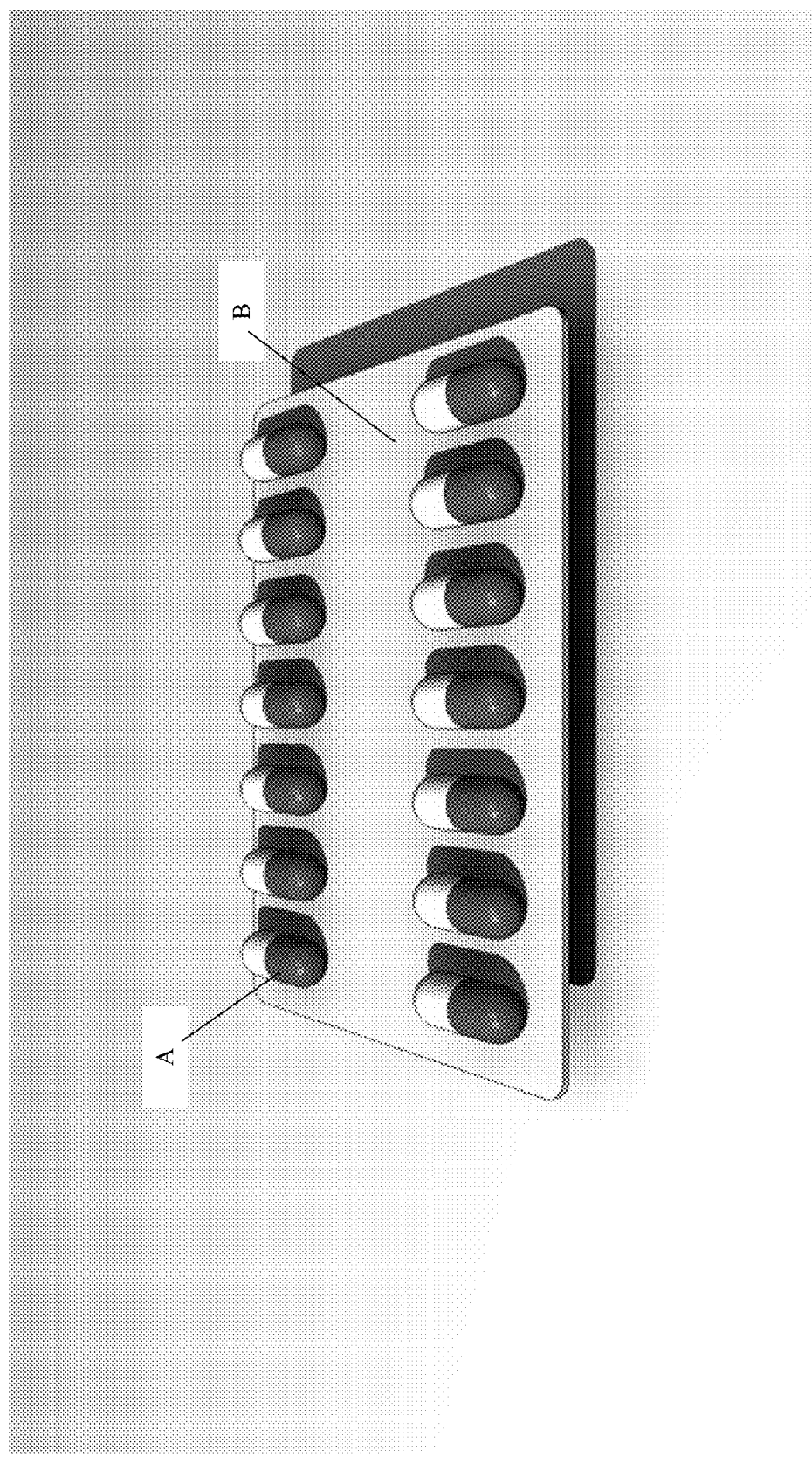
FIG. 10 shows in perspective view a typical blister pack with fourteen pills.

In the examples described hereinafter, reference will always be made to a typical blister pack for pills like the one illustrated in FIG. 10, having a plurality of cells each containing a pill, closed on the bottom by the usual push-through aluminium foil.

Figure 1:
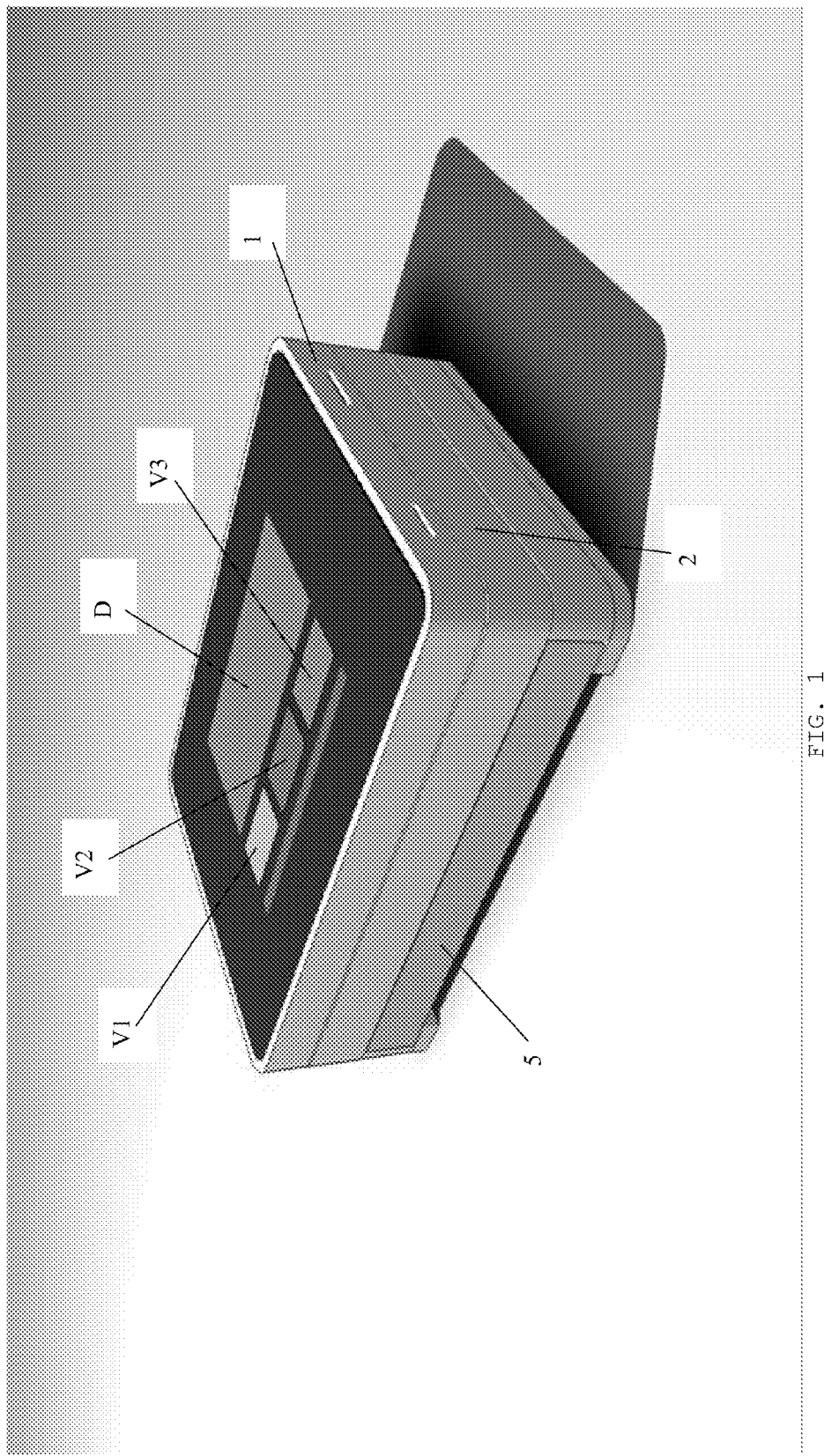
FIG. 1 is a schematic illustration of a first embodiment of the blister-pack case forming the subject of the invention provided with a raisable lid, in the closed configuration.
Figure 2:
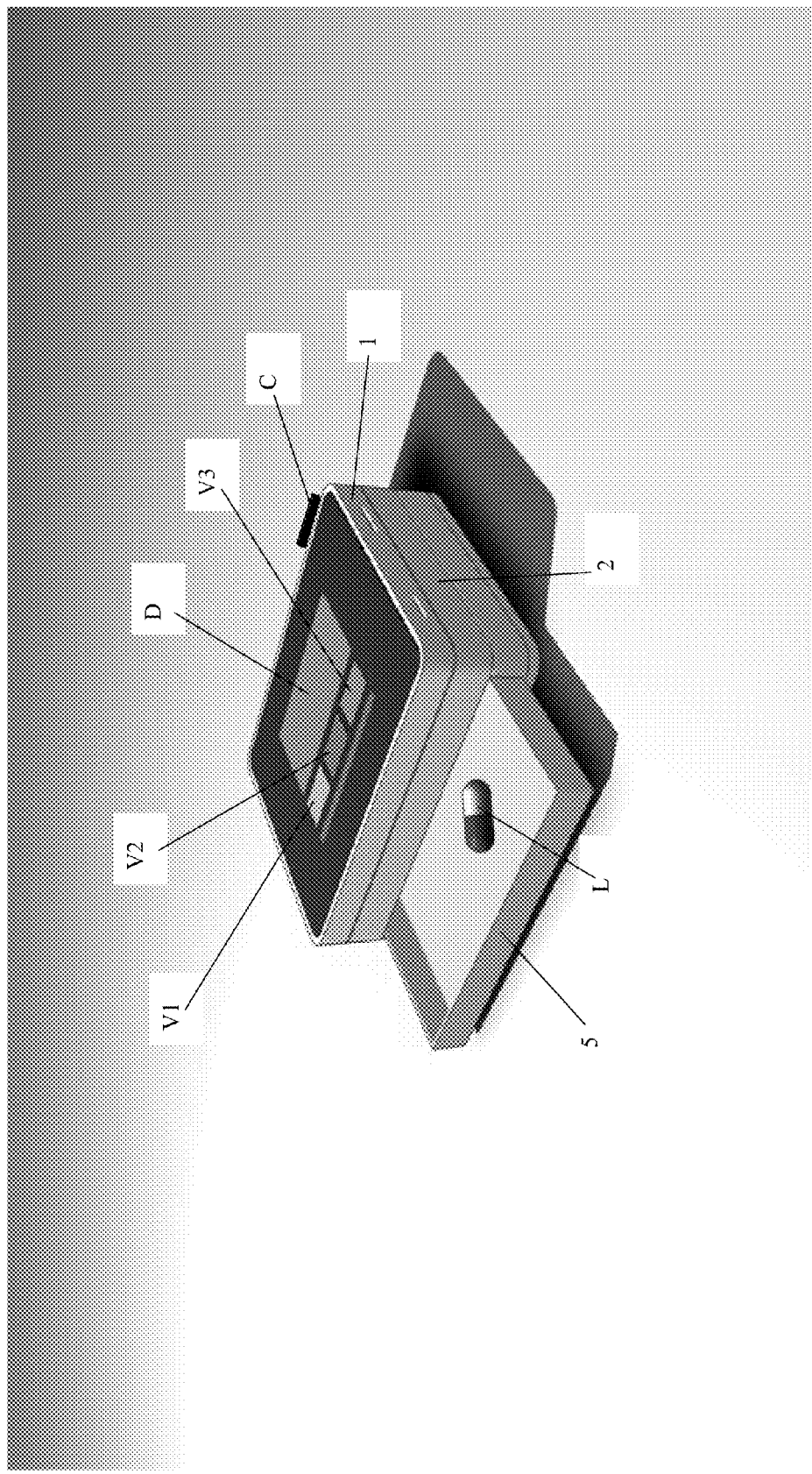
FIG. 2 shows the blister-pack case of FIG. 1 with a drawer, from which it is possible to take the pill, open.
Figure 3A:
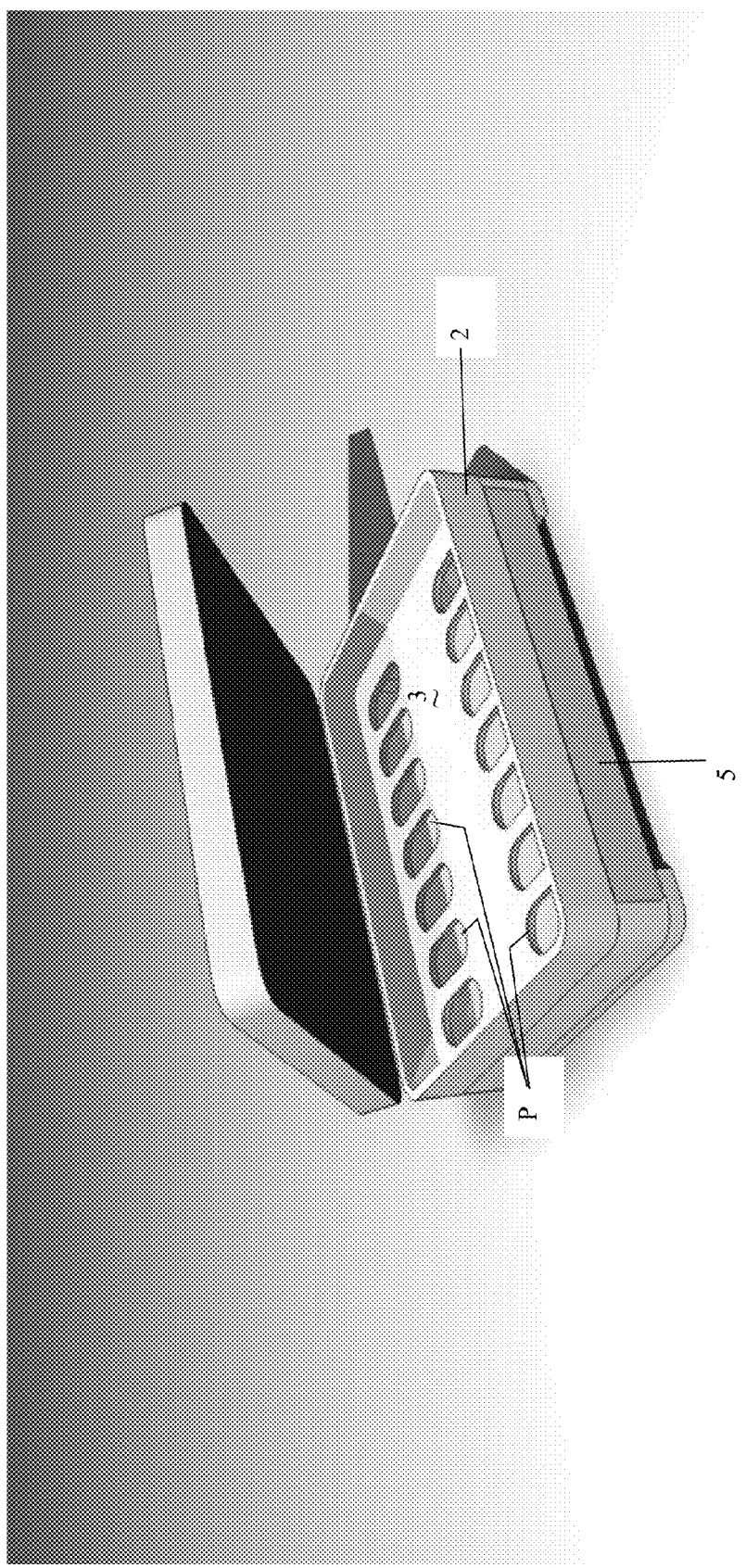
FIG. 3a shows the blister-pack case of FIG. 1 with the lid raised, in the absence of a blister pack.
Figure 3B:
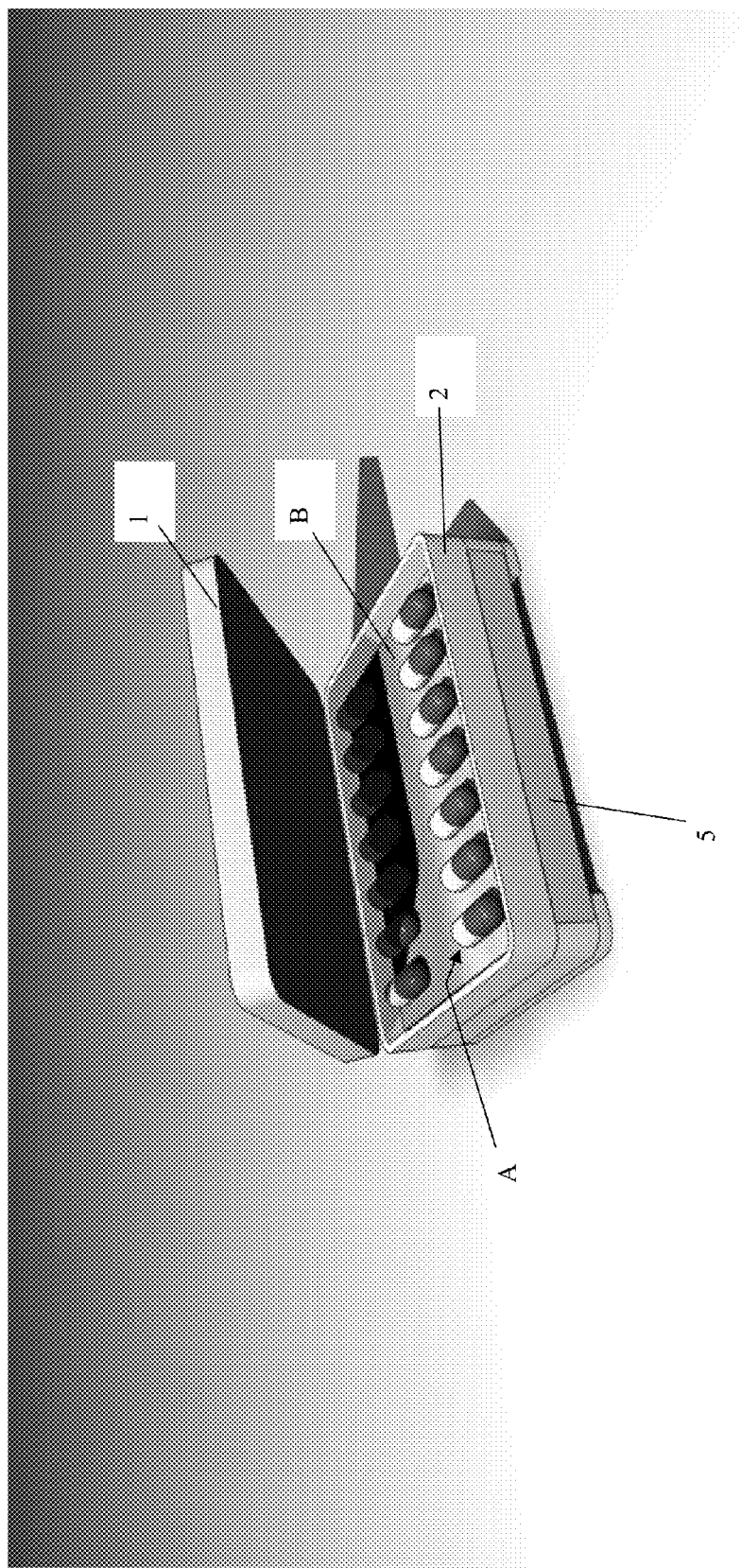
FIG. 3b shows the same blister-pack case with the lid raised but in the presence of a blister pack.
Figure 4:
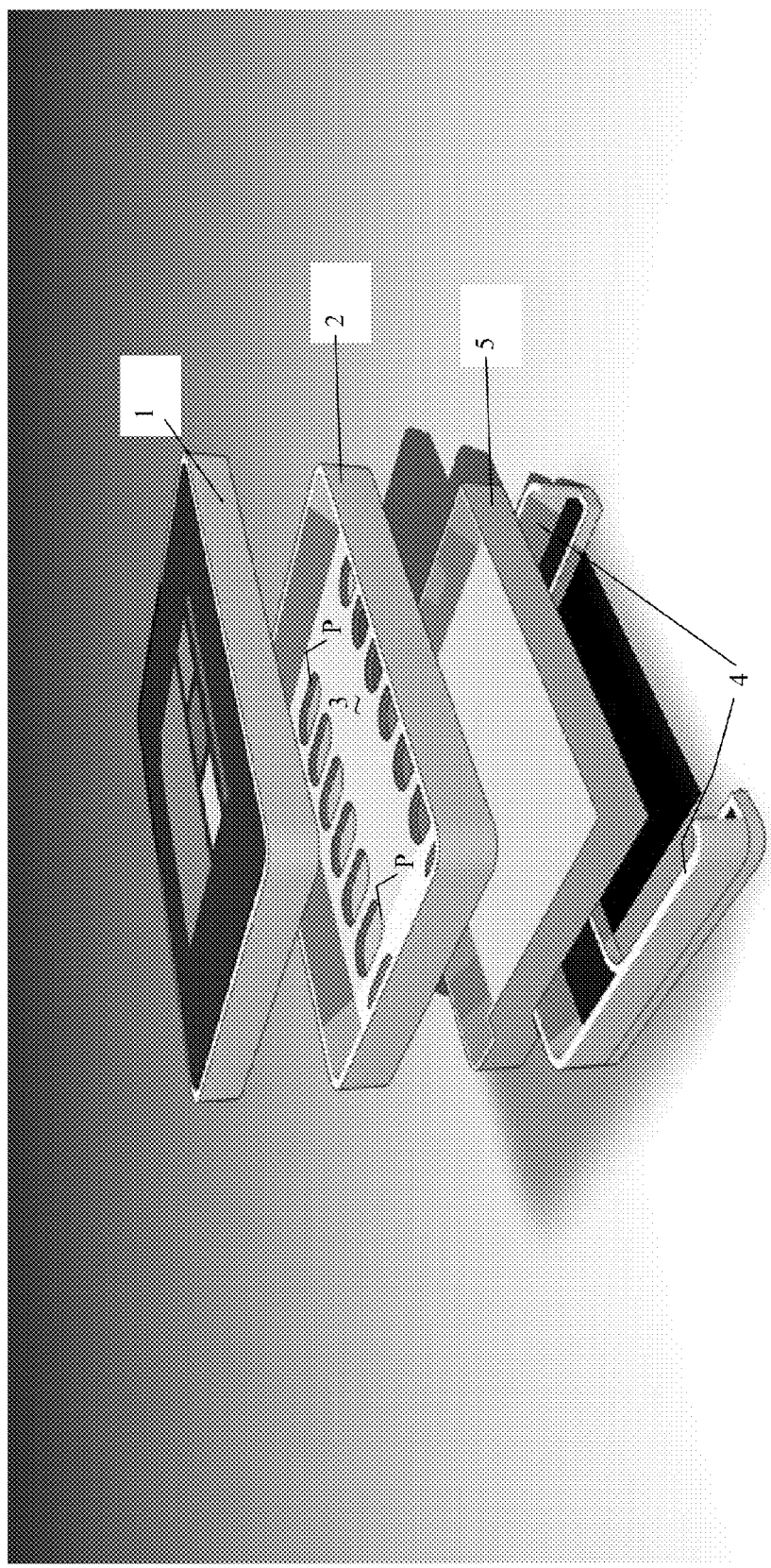
FIG. 4 is an exploded view of the blister-pack case that shows its essential components.
Figure 5:
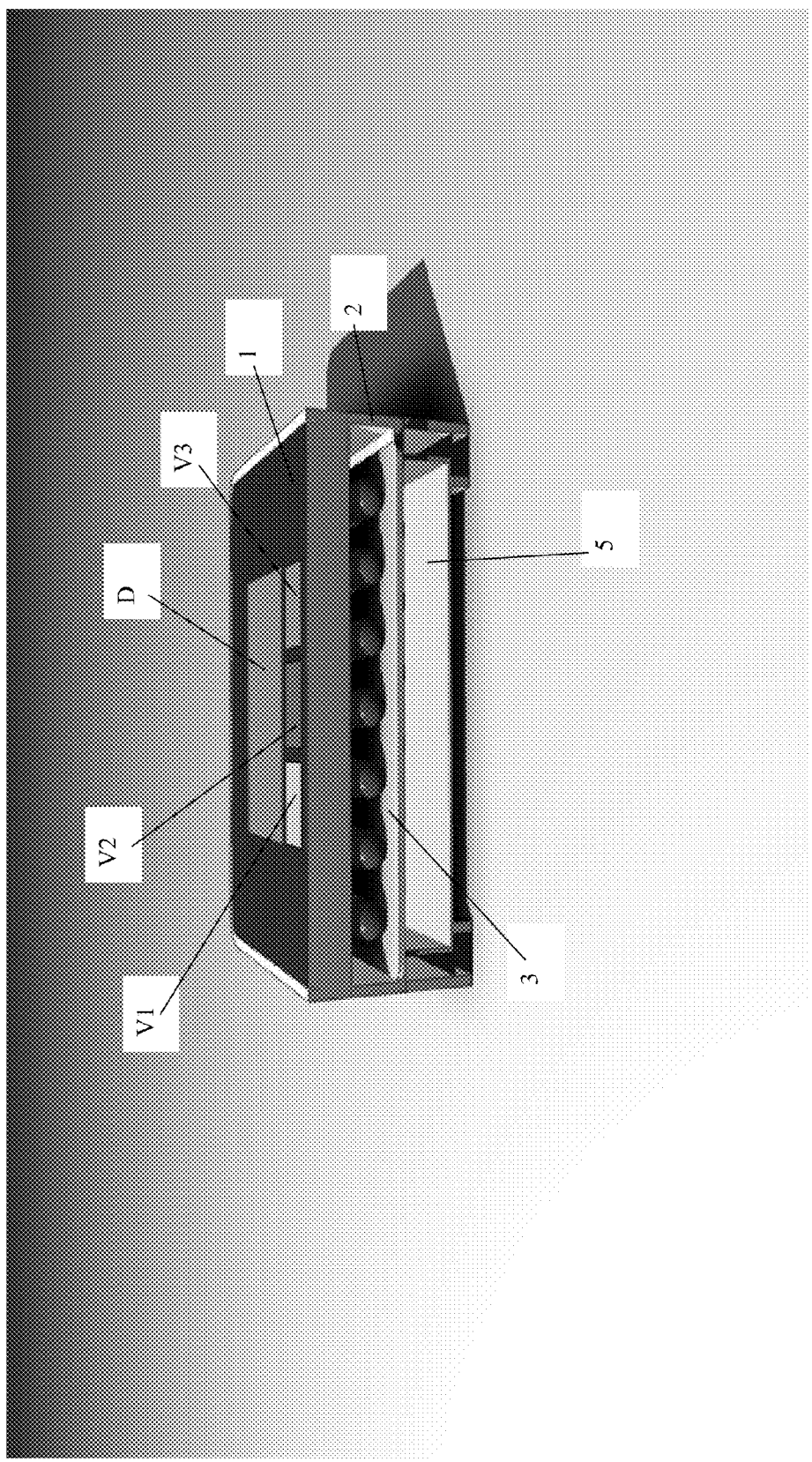
FIG. 5 is a perspective view of the inside of the same blister-pack case containing a blister pack in the absence of the drawer and of the front vertical wall.
Figure 6:
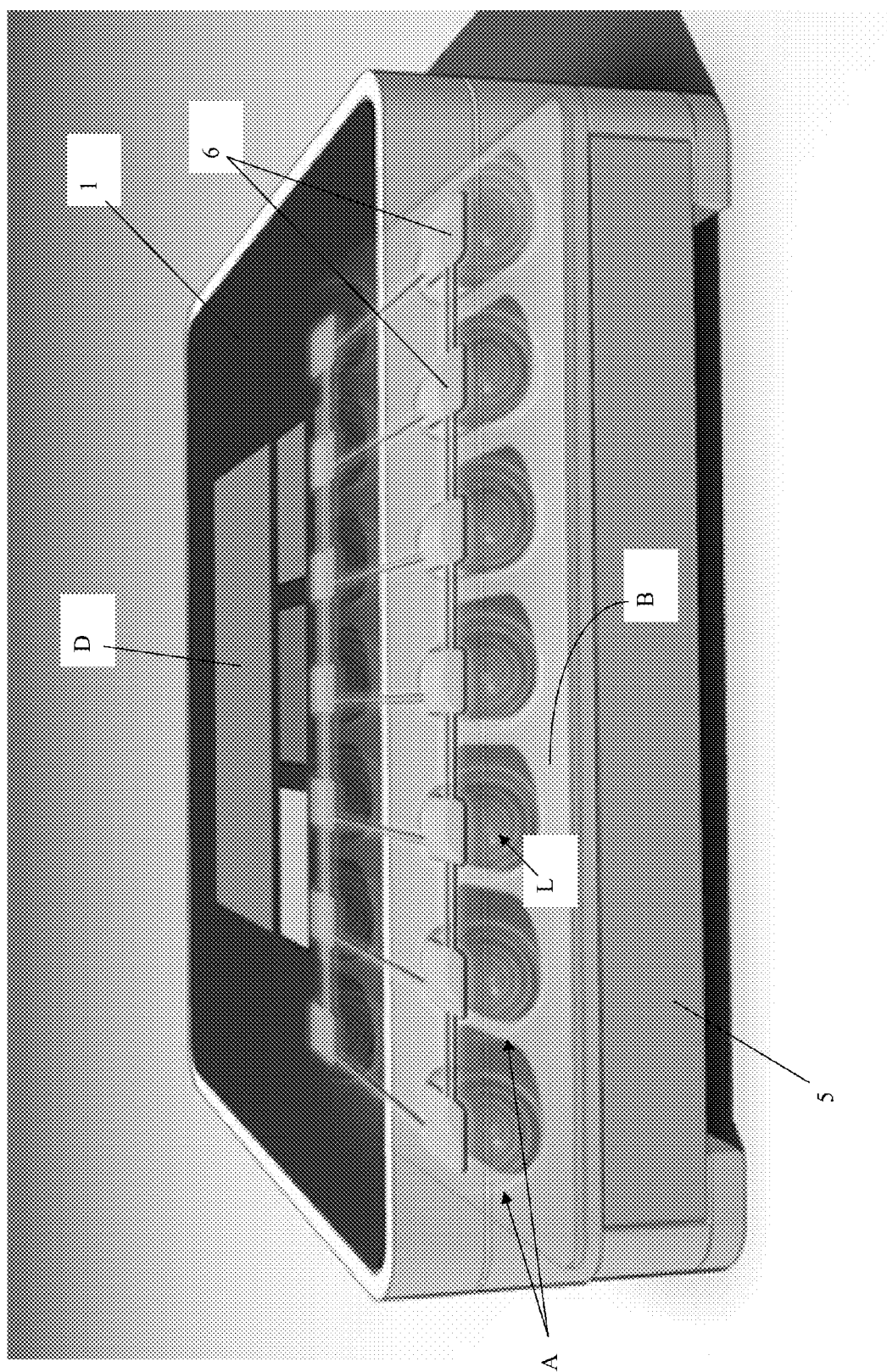
FIG. 6 is a front perspective view of the same blister-pack case closed, which shows in see-through view an array of capacitive sensors arranged in the lid for detecting the presence of the pills in the underlying cells of the blister pack when the latter has been inserted.

With reference to FIGS. 1-9, which illustrate a first embodiment of the invention, the blister-pack case forming the subject of the invention is constituted by a container having a substantially rectangular shape, the dimensions of which are commensurate with those of the blister pack that is to be housed therein. Said container comprises:

a lid 1, which is provided on its top face with a display D for display of the number of pills taken out and possibly the time and date when each pill was taken out, as well as a pushbutton C for turning on said display; made in the thickness of the lid is a seat S for housing an orderly arrangement or array of capacitive sensors 6, each of which is set in a position corresponding to the respective cells of the blister pack B to be contained in the container; as an alternative, said array 6 is provided directly in the mould in the internal face of the lid facing the blister pack;

an underlying tray 2 with the edges raised, the bottom of which is constituted by a surface 3 for supporting the blister pack B and is provided, like a grid, with a plurality of windows or through holes P, which open at each cell of the blister pack B so as to enable each pill, when the corresponding deformable cell A is squeezed, to drop down; insertion of the blister pack B in the blister-pack case is signalled thanks to two switches 13 set at the opposite side ends of the tray that are in contact with the bottom of the blister-pack case, or possibly positioned on two lateral guides that regulate insertion of the blister pack into the tray;

a compartment 4, underlying said tray 2, which is occupied by a drawer 5 that collects each pill L, which, once extracted from the respective cell of the blister pack B, drops through the respective hole of the supporting surface 3; said drawer 5 can be slid out, as may be seen in FIG. 2, to allow the user to take the pill L out of the blister-pack case; each time the drawer 5 is opened, this is signalled by electrical contacts 11 appropriately arranged on the bottom wall of the drawer, which issue, according to the known art, a signal to the central processing unit that manages operation of the device, as described hereinafter.

In the lid 1, which is preferably hinged to the tray 2, at least one seat is provided for housing at least one battery BT for supply of the blister-pack case, said seat being preferably located close to the display D.

Once said battery, which can be of a rechargeable type, is inserted, the blister-pack case is ready for use and is activated by pressing the lateral on/off pushbutton C.

The display D is designed to set itself in energy-saving or stand-by mode after a pre-set time.

Figure 7:
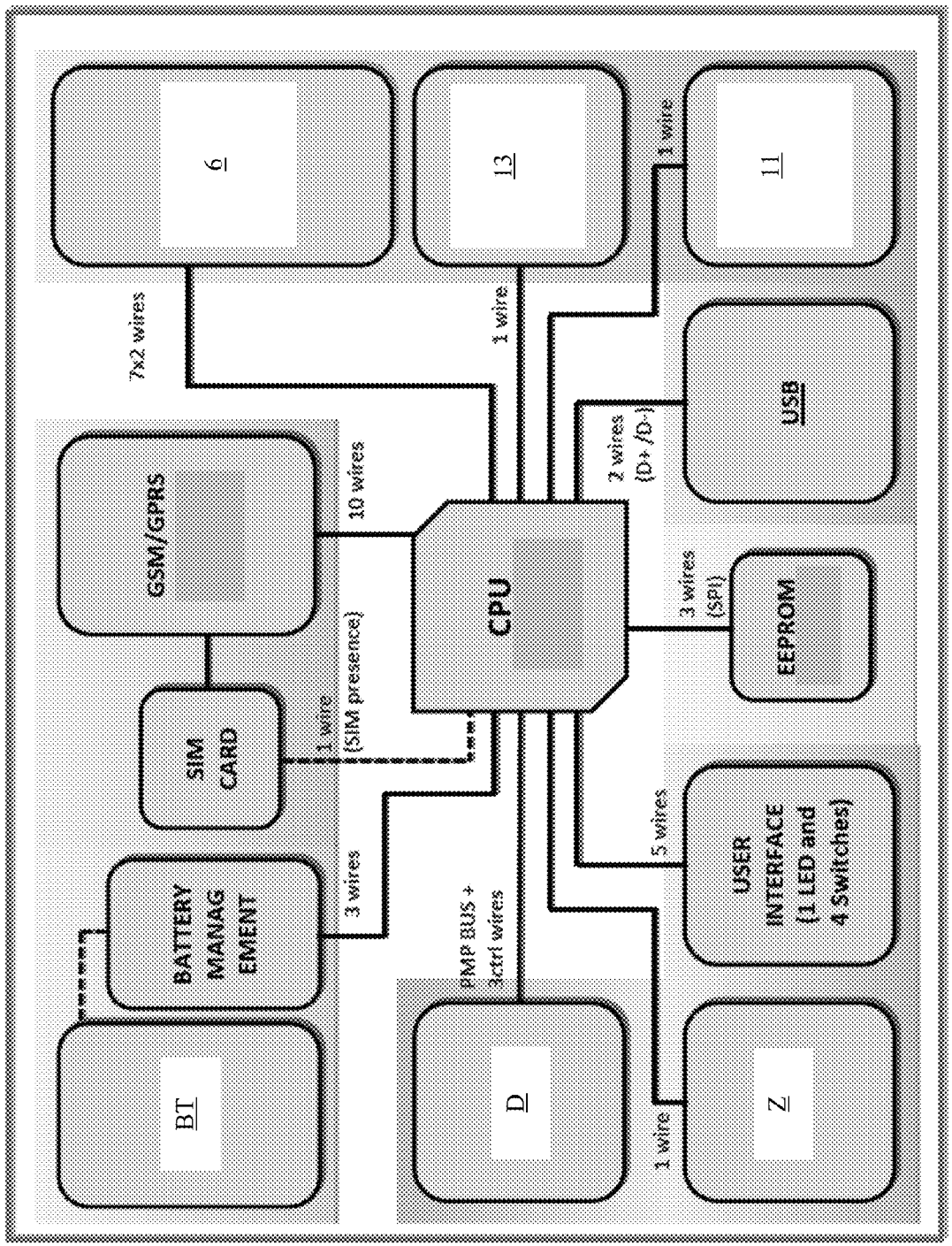
FIG. 7 is a block diagram of the blister-pack case.
Figure 8:
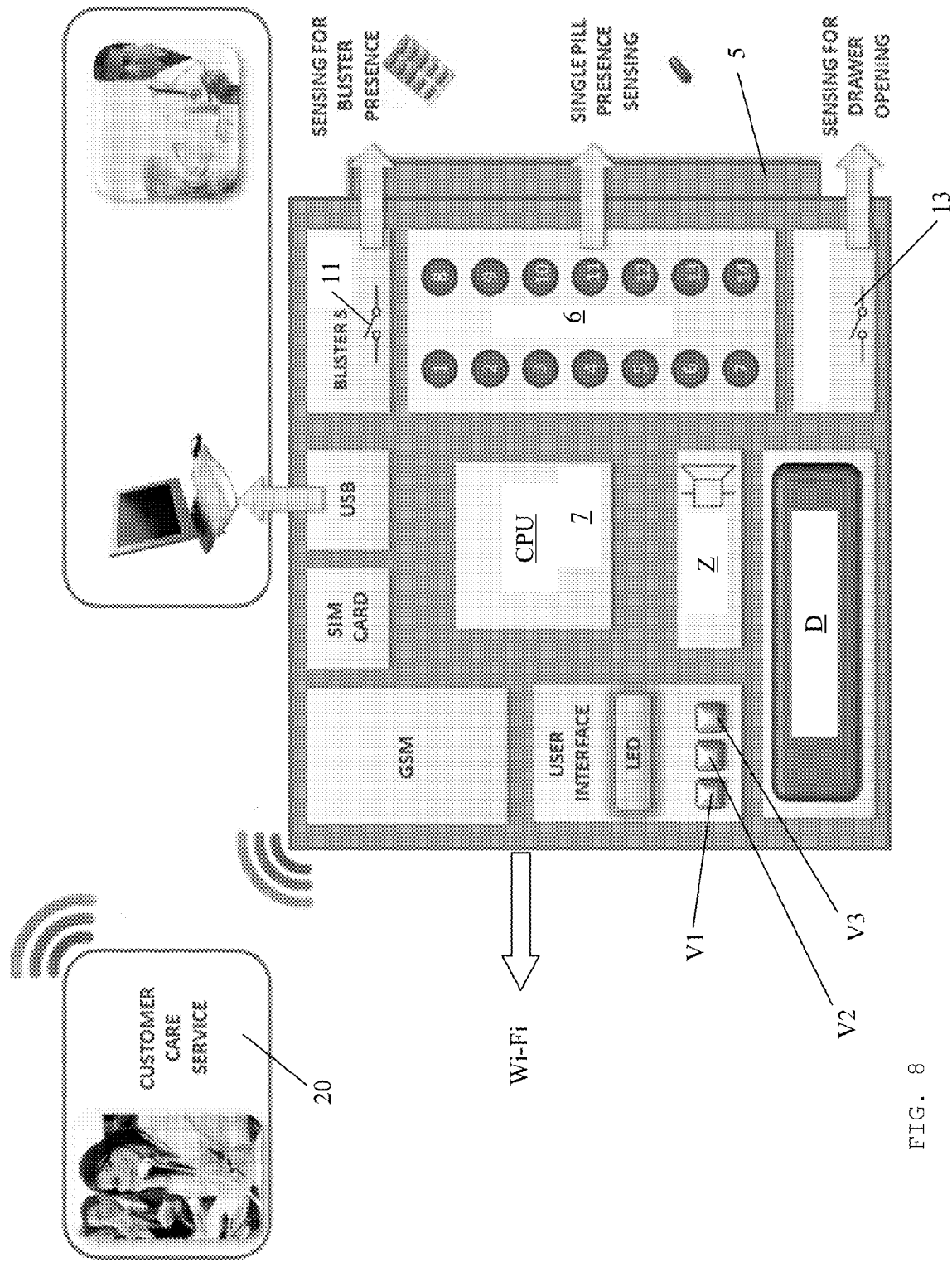
FIG. 8 is a schematic illustration of the arrangement of the sensors designed to detect the presence of the blister pack in the blister-pack case, of the pills in the blister pack, and opening of the drawer.

Moreover contained in the lid 1 is the set of electronic components necessary for operation of the blister-pack case. Said components comprise, as illustrated in FIG. 7, a central processing unit (CPU) designated by 7, which receives and processes the data coming both from the orderly arrangement of capacitive sensors 6 and from the switches 11 that detect the presence of the blister pack in the blister-pack case and from the switches 13 that count the number of times the drawer 5 is opened and closed, and displays said information on the display D, according to the known art. Moreover provided is at least one memory M for storage of information, such as, for example, the number of pills L taken out, the date and time when each pill L is taken out, the number of pills L that remain in the blister pack B, etc.

In order to signal to the user when he/she has to take a pill L, it is possible to envisage that the lid is equipped with an acoustic warning device Z designed to issue an acoustic warning upon command from the timer of the CPU.

Following upon said warning, the patient merely has to lift the lid of the blister-pack case and exert an appropriate pressure on one of the cells of the blister pack containing a pill, up to expulsion of the pill or tablet contained therein, causing it to drop into the drawer 5. At this point, after re-closing the lid, the patient opens the drawer 5, takes out the pill or tablet and re-closes the drawer. Once the drawer is re-closed, the absence of the pill will be signalled by the capacitive array 6, and the datum will be communicated to the CPU, which sends it to appear automatically on the display D.

Constituting an advantageous characteristic of the invention is the fact that the array of capacitive sensors is located in the lid of the blister-pack case. In fact, given that said array is in operative conditions only when all the sensors that make it up are in contact with, or in any case at one and the same identical short distance from, the blister pack, properly arranged on the grid 3, it follows that operation of said array is dependent upon closing of the lid. This makes it possible to prevent drugs that are potentially dangerous for children or in any case highly toxic for persons for whom the therapy is not prescribed, from being taken out easily if the lid of the blister-pack case is inadvertently left open.

There has moreover been designed a resident software that regulates the modalities of assumption of the drug and the relevant controls as described in what follows.

Once the blister pack has been positioned correctly on the grid 3, the array or the orderly arrangement of capacitive sensors 6 detects the presence or otherwise of one or more pills, only following upon a consensus represented by closing of the lid 1 and by opening and subsequent closing of the drawer 5. Only if said conditions are satisfied is said orderly arrangement of capacitive sensors 6 activated and able to detect the absence of one or more pills or capsules in the corresponding cells. In this way, there is the guarantee that a pill L up to then present in the blister pack has been expelled and taken from the drawer 5 and that both the lid and the drawer have been brought into the initial closing condition, preventing persons for whom the therapy was not prescribed from possibly coming into contact with the drug.

For greater protection, means in themselves known are moreover provided, both of a mechanical and an electrical type, designed to prevent opening of the lid and access to the blister pack, controlled by the timer of the CPU so as to be disabled only when the time of assumption has arrived.

Opening remains enabled for a pre-set time window or until the patient takes the drug. It is thus possible to program that for the entire time elapsing between one assumption and the next the container cannot be opened by any unauthorized person unless the block on closing is removed by entering an electronic key or a keyword.

In this different embodiment, extraction of the pills or tablets is performed in the same way: operation of the array 6 is enabled only following upon opening and closing of the lid 1 and opening and closing of the drawer 5. Consequently, the display D will automatically present the updated data of the number of pills or tablets taken at the moment when the blister-pack case is perfectly closed.

Advantageously, the resident software is designed to indicate to the patient also the number of remaining tablets, with their corresponding positions in the blister pack. Through the command pushbuttons present on the lid of the blister-pack case, the patient will be able to check, via the display, the exact position of the pills that he still has to assume, together with the date and time of the last pill taken.

It is moreover possible to envisage that the blister-pack case is able to indicate the percentage of compliance to the therapy linked to the type of pills that the person has to take. Said percentage of compliance is understood as the ratio between the number of pills L that said person, using the blister-pack case, should have taken starting from the day on which the blister-pack case was turned on and the effective number of pills L taken out of the blister pack B starting from the same day. For example, if a hundred days have elapsed since the user last turned on the blister-pack case, and only twenty pills have been taken out of the blister pack B, there will appear on the display D a percentage of compliance of 20% with respect to a dosage of one pill per day.

Calculation of the percentage of compliance is made by the CPU itself, which reads the data stored in the memory and performs said calculation on demand.

To display said percentage of compliance, it is sufficient to keep the display pushbutton V1 in the proximity of the display D depressed (FIG. 1) for a few seconds, or alternatively provide on the lid 1 a further pushbutton not represented in the figures.

Moreover provided on the blister-pack case are another two pushbuttons V2 and V3 distinguished by different colours. The first pushbutton V2, which may for example be red, is used for sending an alert signal requesting an examination by a nurse from the control centre, and the second pushbutton V3, which may for example be green, is used by the patient to send a confirmation to the control centre that a given request has been met.

Figure 9:
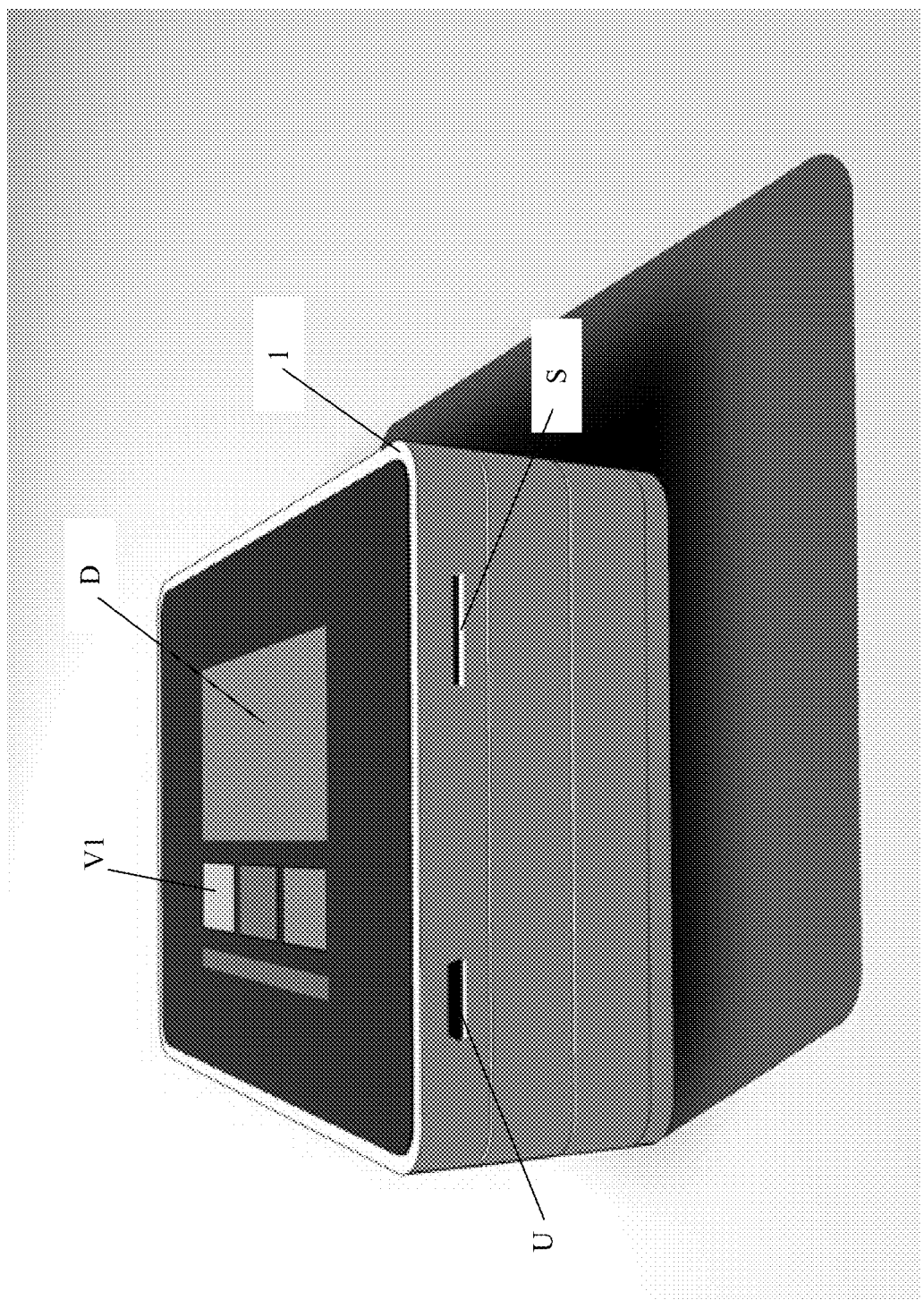
FIG. 9 is a side view of a variant of the blister-pack case according to the invention, which shows a USB output and an input for a SIM card.

According to the variant of FIG. 9, the blister-pack case is equipped with a seat for housing an extractable memory card of a known type, which can be taken out and read by any means of a known type, such as for example a computer or even a cellphone.

Advantageously, the data present in the memory of the blister-pack case can be copied and/or transferred onto said memory card, or vice versa.

In addition, the data present in the memory card can be transferred and/or copied into the memory of said computer, with the dual advantage of loading a copy of the data into a further medium and of being able to obtain a historic file regarding the pills taken out, i.e., the date and time when each pill was taken out.

Yet a further advantageous characteristic is that further data can be transferred and/or copied from said computer or cellphone into said memory card. Consider, for example, a person who takes pills for stabilizing his own pressure; the data regarding the values of his blood pressure together with the date and time when the pressure was measured can be transferred and/or copied into said memory card so that on the display D of the blister-pack case it will be possible to display, not only the date and time when each pill was taken out, but also the date and time of the pressure values.

According to the invention, it is moreover envisaged that the blister-pack case is provided (FIG. 9) with a USB port, designated by U, for enabling a user to connect it, via a purposely provided cable, to any external device, such as for example a computer. It is evident that also in this case it is possible to transfer and/or copy the data from the blister-pack case to said device, or vice versa.

The solution described so far envisages use of detection systems of a capacitive type.

Figure 13:
FIG. 13 is a perspective view of a blister-pack case, to be used with the schemes of FIGS. 11, 12a and 12b, provided only with a drawer, open on the left side.

In the case where the cells housing the capsules of the blister pack are made out of a sheet of transparent material and only the bottom is made of aluminium, also a second embodiment can be used that resorts to the use of an optical system for detecting the presence of the capsules, schematically illustrated in FIG. 13.

Figure 11:
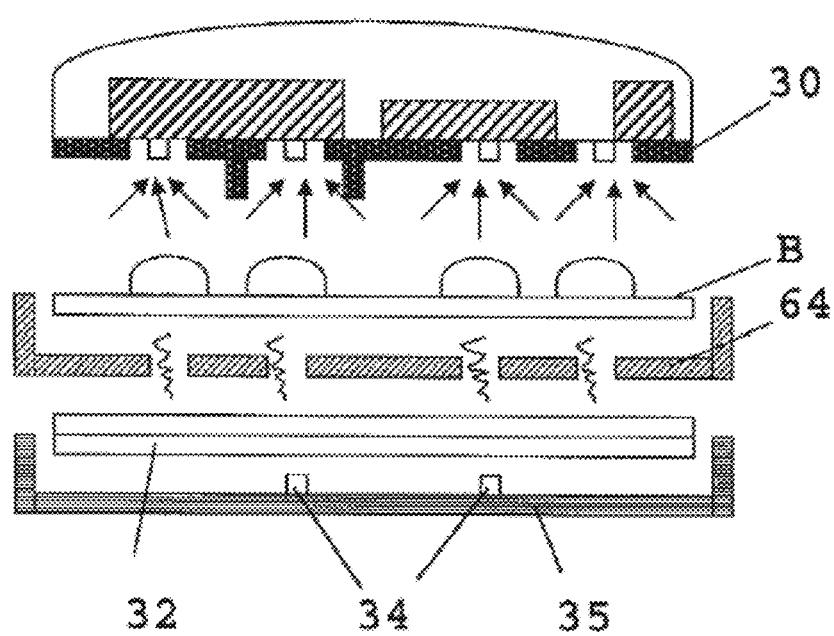
FIG. 11 is a schematic illustration of a second embodiment of a blister-pack case, provided only with a drawer, to be used when the cavities or cells for the capsule are transparent or semitransparent: an optical detection system with impulsive light is used.

As may be seen in this figure, the blister-pack case is equipped with a sliding drawer that can be pulled out on either side, and the means for detecting the presence/absence in the blister pack B of each individual tablet or pill are of an optical type and comprise, according to the diagram of FIG. 11:

a fixed array of SMD LEDs 30 set in the container on the roof of the blister pack B in a position corresponding to each capsule;

a light diffuser, such as for example a semitransparent glass 32 underlying the blister pack;

a certain number of emitting LEDs 34, arranged underneath said glass or alongside it; and further down, a reflecting lamina 35 designed to reflect the light emitted by the LEDs in the direction of the blister pack.

Said emitting LEDs 34 are connected to a charge-pump circuit that is activated whenever the sliding drawer is closed so as to generate an impulsive light of a flash type.

If the housing of the tablet is intact, there is no passage of light and hence the corresponding LED of the overlying array of receiving LEDs 30 is not stimulated.

If, instead, a housing of the blister pack is perforated and the tablet is absent, the passage of light causes in the sensing LEDs 30 emission of a current pulse, which, appropriately amplified, is detected by a micro-controller. The CPU then disables the LED itself to prevent any further warnings.

A third embodiment is illustrated in FIGS. 12a to 15.

Figure 12A:
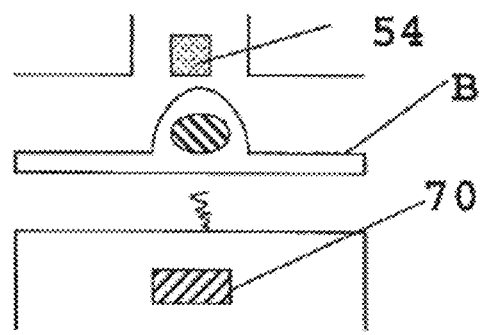
FIGS. 12a and 12b are schematic illustrations of operation of a third embodiment of the invention, with a blister-pack case provided only with a drawer, and an optical detection system with sensors and infrared emitting LEDs, aligned with one another.
Figure 12B:
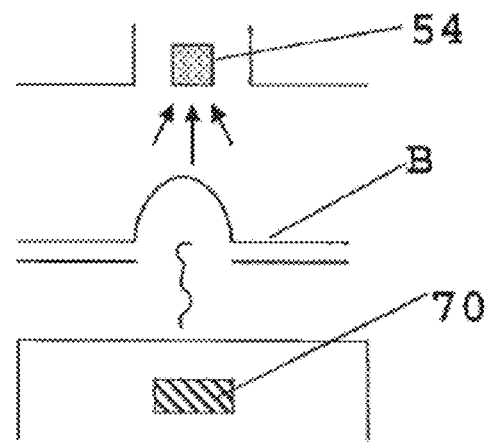

FIGS. 12a and 12b are schematic illustrations of the operation: the blister pack B is positioned in a perforated drawer between a first array of emitting LEDs and a second overlying array of sensing LEDs. If the housing of the tablet is intact, there is no passage of light and hence the top LED is not stimulated. In the case where the blister pack has its aluminium foil perforated and no tablet is present there is passage of light, which will cause in the sensing LED the emission of a current pulse, which, appropriately amplified, is detected by the micro-controller.

Figure 14:
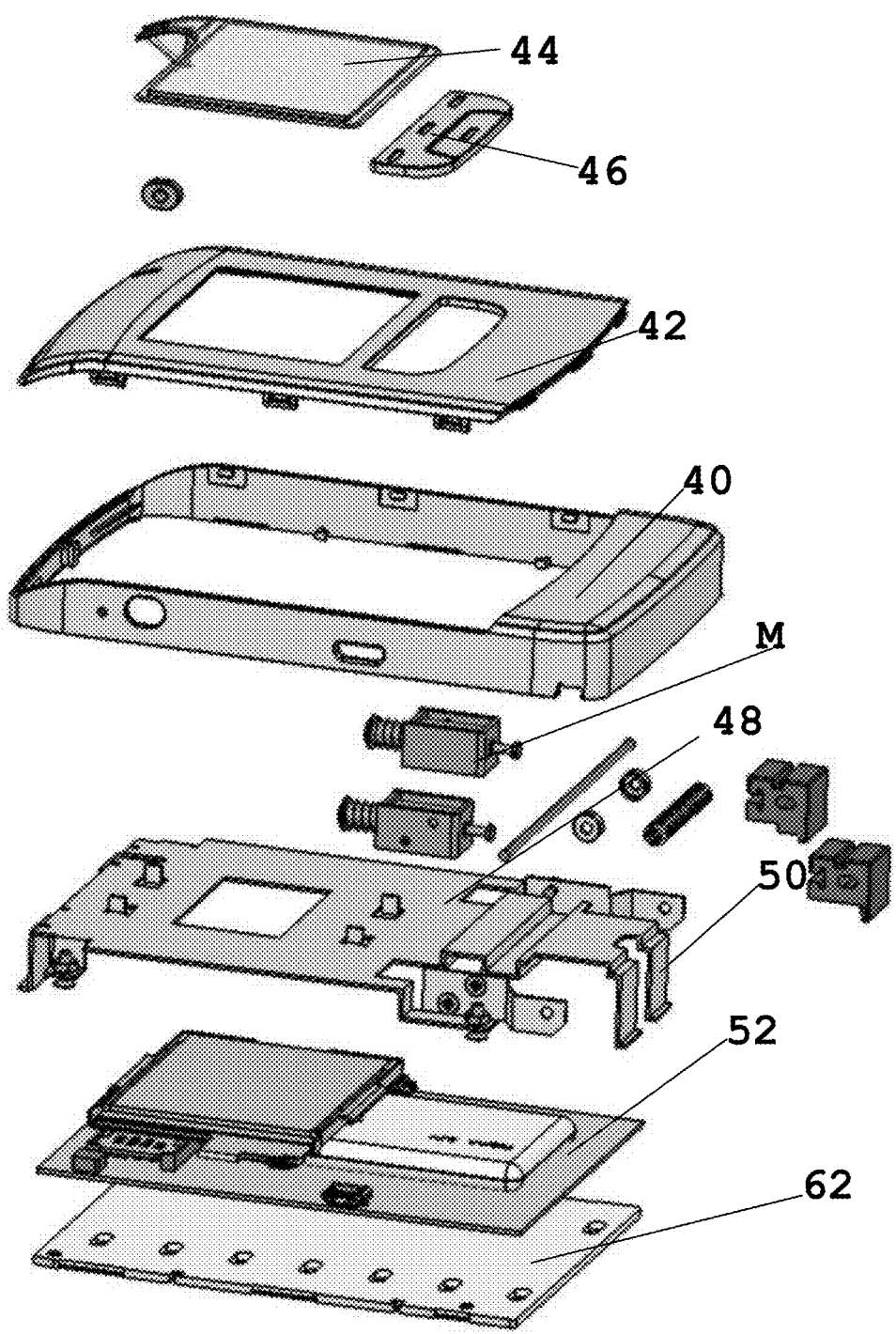
FIG. 14 is a view at an enlarged scale of the components making up the top cover and the internal frame that supports the electronics and the GSM-GPRS module of a blister-pack case according to the scheme of FIGS. 12a and 12b.

In a preferred embodiment, as illustrated in FIGS. 14 and 15, the blister-pack case is constituted by the following components, arranged in succession starting from the top:

a top cover 40 mounted on which is a frame 42, which supports the glass 44 and the keypad set 46;

a stiffening metal plate 48 equipped with engagement-release means 50 that engage with corresponding grooves provided on the lateral guides 58, which are in turn fixed via fast-coupling means to the bottom base 60 of the blister-pack case;

a mother board 52 carrying at the top the central processing unit, the SIM and GPRS cards, and the electronics necessary for operation of the entire blister-pack case, whilst mounted on the bottom face according to the SMD technology is a pair of panels of infrared LEDs 54 set in such a way that each LED corresponds to a cell of the blister pack contained in the case;

a first mask 62 made of non-transparent material provided with holes corresponding to said fixed panels, which is set up against the mother board so as to let through only the punctiform light of one LED for each cell of the blister pack;

a drawer 64, which slides in guides 58 and has a bottom provided with openings corresponding to the cells of the blister pack, where the blister pack itself is positioned;

a second mask 66 made of non-transparent material provided with two rows of through holes that overly two panels of receiving sensors 70 set on the face in view of a card 72 on the bottom of the bottom shell 60 of the blister-pack case, leaving them in view, in such a way that the punctiform light emitted by the infrared LEDs 54 will impinge upon the receiving sensors 70 whenever a pill is taken out.

The device is completed by a pair of motors for enabling opening of the drawer on the right and on the left, the movement being automatic or governed by a pushbutton.

It should be pointed out that the embodiment now described enables, in the case of blister pack totally made of aluminium, the use of capacitive sensors set up against the cells of the blister pack, in this case avoiding the use of arrays of receiving sensors. In fact, given the reduced thickness of the blister-pack case, just one panel or array of capacitive sensors positioned on the roof of the drawer is able to detect the presence or otherwise of the pill in the blister pack located in the drawer itself.

From what has been so far said the numerous advantages of the invention are evident.

A first advantage, as already mentioned, is that the blister-pack case forming the subject of the invention performs the function both of warning the user of the need to take the drug, according to the medical prescription, and of presenting, at any moment, on a display, a set of information useful for the user, such as, for example, the number of pills that should have been taken out of the blister pack up to that moment, and the date and time when the patient last took the drug so that the user can easily realize whether he/she has forgotten or otherwise to take a pill.

A second advantage is represented by the fact that the invention, with a weight and a overall dimensions that are so small that it can be carried in a pocket without any trouble to the user, can contain a GSM/GPRS module, and this enables the Customer Service 20 (FIG. 8) to check remotely and in real time compliance of the patient with the therapy prescribed, even when he/she is away from home.

Another advantage is that in a context of safeguard of children, a plurality of solutions are envisaged that render non-authorised extraction of the drug extremely difficult.

It is possible to envisage that the blister-pack case is equipped with means for enabling data transfer in Bluetooth™/Wi-Fi mode so that the data can be transferred from the blister-pack case to any external device equipped with Bluetooth™/Wi-Fi connection.

It is evident that in this case it is preferable for the blister-pack case to be equipped with an input for insertion of a power-supply plug.

In addition, it is emphasized that the blister-pack case can receive, through a USB port or in Bluetooth™/Wi-Fi mode, data coming also from external apparatuses (such as blood-pressure meters, thermometers, etc.) in such a way that the CPU can integrate them with the data regarding assumption of the drug to create files of daily medical records.

The present invention has been described and illustrated according to some preferred embodiments, but it is understood that equivalent modifications and/or replacements may be made by any person skilled in the branch, without thereby departing from the sphere of protection of the present industrial patent right.

For example, in a first variant of the second embodiment, the memory can be of an extractable type.

Finally, in a further variant, it is possible to envisage that the switch designed to detect extraction of each pill L activated by the drawer 5 when it is opened or closed is mounted in the bottom part of the lid 1 at a portion that comes to bear upon the raised edge of said drawer 5, the reason for this being to confine all the electronic components inside the lid itself.

The invention claimed is:

1. A blister-pack case designed to receive a blister pack having a plurality of deformable cells, each of the cells containing a tablet or a pill and a push-through surface, the blister-pack case comprising:
a container with an internal compartment closable and accessible from outside in which the blister pack is inserted or rests with a push-through surface on a surface of a grid having a plurality of through holes in such a way that each of the cells corresponds to a respective hole of the grid,
a display on the container,
a detection means that detects a presence or an absence of the pill or the tablet, the detection being made at a time and a date, the detection means comprising i) an optical means with receiving means and emitting means or ii) capacitive means, the detection means being located above and/or underneath said grid, the detection means designed to detect the presence or the absence of the pill or tablet when dropped from an overlying one of the cells following upon pressure that a user exerts on said deformable cell of the blister pack,
a resident memory,
a central processing unit operatively connected to the detection means and to the resident memory, data collected by said detection means being sent to the central processing unit for processing and storing said data together with the time and the date of the detection in the resident memory, the central processing unit displaying stored data on the display,
wherein said container includes at least one of i) an autonomous power and ii) an input for enabling insertion of a plug of a power supply,
a raisable lid, wherein the internal compartment is accessible through the raisable lid,
a drawer provided underneath said grid, wherein drawer can be pulled out horizontally and the pill or the tablet taken from the drawer, the drawer designed to receive the pill or the tablet that drops from the overlying cell, and
a further detection means provided on the drawer, the further detection means for detecting a number of times the drawer is opened and closed on said drawer.

2. The blister-pack case according to claim 1, further comprising means designed to transmit, via a packet mobile-radio interface, the data detected by the central processing unit to an authorized remote control center, which can in turn dialogue with a patient via at least one of the group consisting of i) packet mobile-radio interface and ii) circuit mobile-radio interface.

3. The blister-pack case according to claim 1, wherein said display is positioned on a top wall of the container.

4. The blister-pack case according to claim 1, wherein said capacitive means are constituted by an orderly distribution or array of sensors for capacitive detection of the presence of each of the pills or the tablets of the blister pack (B), each said sensor being positioned in the lid at each hole of the grid.

5. The blister-pack case according to claim 1, wherein the lid comprises an acoustic warning device designed to emit an acoustic warning upon command from the central processing unit.

6. The blister-pack case according to claim 1, wherein the display is positioned on said lid and said display is designed to present an updated number of pills taken out of the cells and/or other information regarding the pills taken out, which are processed by the central processing unit.

7. The blister-pack case according to claim 4, wherein a resident software is provided that is executed by the central processing unit according to signals received regarding closing of the lid and the opening and the closing of the drawer, which enables operation of the array of capacitive sensors that detect at each operation extraction of one or more of the pills.

8. A blister-pack case designed to receive a blister pack having a plurality of deformable cells, each of the cells containing a tablet or a pill and a push-through surface, the blister-pack case comprising:
a container with an internal compartment closable and accessible from outside in which the blister pack is inserted or rests with a push-through surface on a surface of a grid having a plurality of through holes in such a way that each of the cells corresponds to a respective hole of the grid,
a display on the container,
a detection means that detects a presence or an absence of the pill or the tablet, the detection being made at a time and a date, the detection means comprising i) an optical means with receiving means and emitting means or ii) capacitive means, the detection means being located above and/or underneath said grid, the detection means designed to detect the presence or the absence of the pill or tablet when dropped from an overlying one of the cells following upon pressure that a user exerts on said deformable cell of the blister pack,
a resident memory,
a central processing unit operatively connected to the detection means and to the resident memory, data collected by said detection means being sent to the central processing unit for processing and storing said data together with the time and the date of the detection in the resident memory, the central processing unit displaying stored data on the display,
wherein said container includes at least one of i) an autonomous power and ii) an input for enabling insertion of a plug of a power supply,
wherein said processor is designed to read the data from the resident memory and perform a calculation of a percentage of compliance to a therapy linked to a type of the pills that a person has to take, said percentage being a ratio between a number of pills that the person should have taken out of the blister pack starting from a day on which the blister-pack case was reset at a time of a new cycle of therapy, and a number of pills effectively taken out of the blister pack starting from the day on which the blister-pack case was reset.

9. The blister-pack case according to claim 1, further comprising at least one of the group consisting of i) a USB port (U) and ii) means for transfer of data in Bluetooth™/Wi-Fi mode in order to enable the user to interface with other devices.

10. The blister-pack case according to claim 1, further comprising a light-warning device designed to emit a light warning upon command from said central processing unit to warn the user to take a product and/or when a number of pills remaining in the blister pack is below a pre-set number.

11. The blister-pack case according to claim 1, wherein a resident software is provided designed to request, during setting, a body weight of a patient to process a proper dosage of the pill or the tablet.

12. A blister-pack case designed to receive a blister pack having a plurality of deformable cells, each of the cells containing a tablet or a pill and a push-through surface, the blister-pack case comprising:
   a container with an internal compartment closable and accessible from outside in which the blister pack is inserted or rests with a push-through surface on a surface of a grid having a plurality of through holes in such a way that each of the cells corresponds to a respective hole of the grid,
   a display on the container,
   a detection means that detects a presence or an absence of the pill or the tablet, the detection being made at a time and a date, the detection means comprising an optical means with receiving means and emitting means located above and underneath said grid, the detection means designed to detect the presence or the absence of the pill or tablet when dropped from an overlying one of the cells following upon pressure that a user exerts on said deformable cell of the blister pack,
   a resident memory,
   a central processing unit operatively connected to the detection means and to the resident memory, data collected by said detection means being sent to the central processing unit for processing and storing said data together with the time and the date of the detection in the resident memory, the central processing unit displaying stored data on the display,
   wherein said container includes at least one of i) an autonomous power and ii) an input for enabling insertion of a plug of a power supply, wherein,
   for a blister pack with the cells made out of a sheet of transparent material and only a bottom of the cells is made of aluminum foil, the blister-pack case is without a lid and is equipped with an extractable drawer that can slide on either side and has a perforated bottom comprised of the grid, the blister pack being positioned on the grid so that each hole corresponds to one of the tablets or pills,
   the optical means comprise:
   a fixed array of SMD LEDs set in the container on a roof of the drawer where the blister pack is provided in such a way that each LED corresponds to one of the cells,
   a light diffuser positioned underneath the perforated bottom of the drawer in which the blister pack is contained,
   a number of emitting LEDs arranged underneath said or alongside said light diffuser, and
   lower down from the emitting LEDs, a reflecting lamina designed to reflect light emitted by the emitting LEDs in a direction of the blister pack
   said emitting LEDs being connected to a charge-pump circuit that is activated whenever the drawer is closed so as to generate an impulsive flash of light, thus obtaining that, when a cell of the blister pack is perforated and the tablet or the pill is absent, a passage of light will cause in a sensing LED emission of a current pulse, which, is amplified and is detected by a micro-controller, said central processing unit disabling said sensor after the tablet or the pill corresponding thereto has been taken out.

13. A blister-pack case designed to receive a blister pack having a plurality of deformable cells, each of the cells containing a tablet or a pill and a push-through surface, the blister-pack case comprising:
   a container with an internal compartment closable and accessible from outside in which the blister pack is inserted or rests with a push-through surface on a surface of a grid having a plurality of through holes in such a way that each of the cells corresponds to a respective hole of the grid,
   a display on the container,
   a detection means that detects a presence or an absence of the pill or the tablet, the detection being made at a time and a date, the detection means comprising i) an optical with receiving and emitting means or ii) capacitive means, the detection means being located above and/or underneath said grid, the detection means designed to detect the presence or the absence of the pill or tablet when dropped from an overlying one of the cells following upon pressure that a user exerts on said deformable cell of the blister pack,
   a resident memory,
   a central processing unit operatively connected to the detection means and to the resident memory, data collected by said detection means being sent to the central processing unit for processing and storing said data together with the time and the date of the detection in the resident memory, the central processing unit displaying stored data on the display,
   wherein said container includes at least one of i) an autonomous power and ii) an input for enabling insertion of a plug of a power supply, and
   the following components set in succession starting from a top position:
   a top cover mounted on which is a frame that supports a glass and a keypad set,
   a stiffening metal plate equipped with engagement-release means that engage with corresponding grooves made in lateral guides, which are in turn fixed, via fast-coupling means, to a bottom base of the blister-pack case,
   a mother board carrying at a top the central processing unit, SIM and GPRS cards, and electronics necessary for operation of the entire blister-pack case, whilst arranged on the bottom face is a fixed array of infrared LEDs arranged in such a way that each LED corresponds to a cell of the blister pack contained in the case,
   a first mask made of non-transparent material provided with holes corresponding to said fixed array of infrared LEDs set up against the mother board so as to let through only punctiform light of one LED for each cell of the blister pack;

a drawer, which slides in guides and has a bottom provided with the grid, the holes of the grid corresponding to the cells of the blister pack, when the blister pack is positioned on the grid, a second mask made of non-transparent material provided with a plurality of through holes that overly an array of receiving sensors arranged on in view of a card on the bottom of a bottom shell of the blister-pack case, so that punctiform light emitted by each infrared LED impinges upon a corresponding receiving sensor whenever the pill or the tablet set in between has been taken out, and a pair of motors for enabling a movement of opening to a right and to a left of the drawer, which opening is automatic or is controlled by a pushbutton.

* * * * *